United States Patent
Vanatta

(12) 
(10) Patent No.: US 6,684,721 B2
(45) Date of Patent: Feb. 3, 2004

(54) METHOD AND APPARATUS FOR PREPARING A LIQUID SAMPLE

(75) Inventor: Lynn E. Vanatta, Dallas, TX (US)

(73) Assignee: Air Liquide America, L.P., Houston, TX (US)

( * ) Notice: Subject to any disclaimer, the term of this patent is extended or adjusted under 35 U.S.C. 154(b) by 112 days.

(21) Appl. No.: 10/137,640

(22) Filed: May 3, 2002

(65) Prior Publication Data

US 2003/0019307 A1 Jan. 30, 2003

Related U.S. Application Data

(60) Provisional application No. 60/307,884, filed on Jul. 27, 2001.

(51) Int. Cl.[7] ................................................. G01N 1/00
(52) U.S. Cl. ................................... 73/864.81; 73/864.73
(58) Field of Search ......................... 73/863.81, 863.83, 73/864.34, 864.81, 61.56, 61.59, 23.41, 23.42, 864.73, 864.74

(56) References Cited

U.S. PATENT DOCUMENTS

| | | | | |
|---|---|---|---|---|
| 3,638,831 A | * | 2/1972 | Pauwels et al. | 222/1 |
| 4,836,039 A | * | 6/1989 | de Silva et al. | 73/864.81 |
| 5,035,149 A | * | 7/1991 | Wierenga | 73/863.23 |
| 5,286,451 A | * | 2/1994 | De Silva et al. | 422/68.1 |

OTHER PUBLICATIONS

Vanatta, "Quantitation of anions at parts–per–trillion levels in semiconductor pure water by means of a laboratory ion chromatograph"; *Journal of Chromatograph A*, , 739 (1996), pp. 199–205.

* cited by examiner

*Primary Examiner*—Robert Raevis
(74) *Attorney, Agent, or Firm*—Linda K. Russell

(57) ABSTRACT

A method of preparing a liquid sample is provided. The method involves steps of: providing a pressurizable vessel that contains a liquid sample in a container, and a sample tube extending from beneath the surface of the liquid sample to a point outside of the vessel; introducing a purge gas into the vessel through a purge-gas inlet conduit, and simultaneously removing the gas atmosphere in the vessel through a purge-gas outlet conduit, thereby displacing the atmosphere in the pressurizable vessel; and pressurizing the vessel with the purge gas to transfer a portion of the liquid sample from the container through the sample tube. Also provided are apparatuses for preparing a liquid sample, as well as methods and apparatuses for performing an analytical measurement. The invention has particular applicability in liquid-sample preparation for analytical techniques such as liquid and gas chromatography, and solid-phase-extraction, and more specifically to the detection of impurities in a liquid sample, such as in liquid chemicals used in the semiconductor-manufacturing industry.

34 Claims, 4 Drawing Sheets

METHOD AND APPARATUS FOR PREPARING A LIQUID SAMPLE

CROSS-REFERENCE TO RELATED APPLICATIONS

This application claims the benefit under 35 U.S.C. §119 (e) of provisional Application No. 60/307,884, filed Jul. 27, 2001, the entire contents of which are herein incorporated by reference.

BACKGROUND OF THE INVENTION

1. Field of the Invention

The invention relates to novel methods of preparing a liquid sample, and to novel apparatuses for preparing a liquid sample. The invention further relates to novel methods and apparatuses for performing an analytical measurement. The invention has particular applicability in liquid-sample preparation for analytical techniques such as liquid chromatography, for example, ion chromatography, and more specifically to the detection of impurities in a liquid sample, such as in liquid chemicals used in the semiconductor-manufacturing industry.

2. Description of the Related Art

In the semiconductor-manufacturing industry, ultra-high-purity chemicals such as hydrogen peroxide ($H_2O_2$), hydrochloric acid (HCl), nitric acid ($HNO_3$), hydrofluoric acid (HF), ammonium hydroxide ($NH_4OH$) and deionized water, among many others, are employed in processes such as wafer-cleaning and/or etching. It is imperative that the impurity levels in such chemicals be as low as possible, since yields of the semiconductor devices being formed can be adversely affected by the impurities. With current device geometries, the presence of impurities on the parts-per-trillion (ppt) level can be problematic. In light of the foregoing, the analytical techniques used by chemical suppliers and users of the chemicals, such as semiconductor manufacturers, are becoming more critical.

During analysis of the liquid chemical, impurities can be added to the sample by virtue of the analysis technique itself, for example, in manually loading the liquid chemical into the analytical instrument. To prevent such external contamination of the sample, pneumatic loading methods have been developed and are currently employed for liquid-sample introduction into the analytical instrument. An apparatus for performing such function is commercially available, for example, from Dionex Corporation, Sunnyvale, Calif. L. Vanatta, J. Chromatogr. A 739 (1996), pp. 199–205, describes a method and apparatus for pneumatically loading a liquid sample into a liquid chromatograph.

Use of a pressurizable vessel for pneumatically transporting the liquid sample from a sample holder to the analytical instrument inlet has been considered a substantially contamination-free technique for sample loading. In this method, the liquid sample is typically contained in an open sample holder, which is manually placed inside a pressurizable vessel. This placement is accomplished by removing the lid of the vessel, placing the liquid sample on a stage at the bottom of the vessel, and replacing and securing the lid. The vessel includes a gas inlet connected to an inert-gas source, and a liquid-sample conduit extending from the sample holder (below the liquid surface) through the vessel lid. The inert gas is introduced into the vessel, thereby raising the pressure in the vessel and thus the pressure over the surface of the liquid sample. With sufficient pressure, the liquid sample is forced to flow through the sample conduit and into the analytical-instrument sample-loading port.

While the above described method and apparatus can perform adequately for the measurement of certain analytes, particular analytes are problematic in obtaining accurate measurements. In particular, it has been found that analytes that are also present in the atmosphere in which the measurement is being conducted and that have a high solubility in the liquid chemical being measured give rise to inaccurate measurements. This problem is aggravated as the analyte solubility increases with pressurization of the vessel during sample loading.

For example, ammonia is typically present in the laboratory atmosphere in which the sample preparation and measurement are conducted. Ammonia is very soluble in water and, during pressurization of the vessel with the inert gas, the ammonia solubility increases even further. As a result, the ammonia is driven into solution and forms ammonium ions in the liquid sample. In the case where ammonium is the analyte of interest, an accurate measurement of the liquid sample would not be possible because of this artificial increase in ammonium content. The practical effect of this situation is that all blanks, standards, and samples to be measured become contaminated, resulting in inaccurate quantification of impurity levels. Other examples of materials that may pose similar problems are organic solvents, such as alcohols and acetone, which are commonly used in analytical laboratories.

To overcome or conspicuously ameliorate the aforementioned problems associated with the related art, it is an object of the present invention to provide methods of preparing a liquid sample.

It is a further object of the invention to provide methods of performing an analytical measurement.

It is a further object of the invention to provide apparatuses for preparing a liquid sample which apparatuses can be used to practice the inventive methods.

It is a further object of the invention to provide apparatuses for performing an analytical measurement. Other objects and aspects of the present invention will become apparent to one of ordinary skill in the art on a review of the specification, drawings and claims appended hereto.

SUMMARY OF THE INVENTION

According to a first aspect of the invention, a method of preparing a liquid sample is provided. The method comprises: providing a pressurizable vessel that contains a liquid sample in a container, and a sample tube extending from beneath the surface of the liquid sample to a point outside of the vessel; introducing a purge gas into the vessel through a purge-gas inlet conduit, and simultaneously removing the gas atmosphere in the vessel through a purge-gas outlet conduit, thereby displacing the atmosphere in the pressurizable vessel; and pressurizing the vessel with the purge gas to transfer a portion of the liquid sample from the container through the sample tube.

According to a further aspect of the invention, provided is a method of performing an analytical measurement. The method comprises: providing a pressurizable vessel that contains a liquid sample in a container, and a sample tube extending from beneath the surface of the liquid sample to an analytical instrument; introducing a purge gas into the vessel through a purge-gas inlet conduit, and simultaneously removing the gas atmosphere in the vessel through a purge-gas outlet conduit, thereby displacing the atmosphere in the pressurizable vessel; pressurizing the vessel with the purge gas to transfer a portion of the liquid sample from the container through the sample tube; and introducing the liquid sample into the analytical instrument.

According to a further aspect of the invention, provided is an apparatus for preparing a liquid sample. The apparatus comprises: a pressurizable vessel comprising one or more walls, and a plurality of apertures in the walls, the apertures comprising one or more purge-gas inlet apertures and one or more purge-gas outlet apertures; one or more purge-gas inlet conduits connected to the pressurizable vessel in fluid communication with the purge-gas inlet apertures, for introducing a purge gas through the purge-gas inlet apertures; a liquid-sample container for holding a liquid sample inside the pressurizable vessel; a sample tube extending from beneath the surface of the liquid sample in the container to a point outside of the pressurizable vessel for pneumatically transferring the liquid sample from the liquid-sample container to the point outside of the pressurizable vessel.

According to a further aspect of the invention, provided is an apparatus for performing an analytical measurement. The apparatus comprises: an analytical instrument; a pressurizable vessel comprising one or more walls, and a plurality of apertures in the walls, the apertures comprising one or more purge-gas inlet apertures and one or more purge-gas outlet apertures; one or more purge-gas inlet conduits connected to the pressurizable vessel in fluid communication with the purge-gas inlet apertures, for introducing a purge gas through the purge-gas inlet apertures; a liquid-sample container for holding a liquid sample inside the pressurizable vessel; and a sample tube extending from beneath the surface of the liquid sample in the container to the analytical instrument.

The methods and apparatuses in accordance with the invention allow for pneumatic transfer of ultra-high-purity liquid-chemical samples in a manner that can effectively prevent contamination during the transfer process.

BRIEF DESCRIPTION OF THE DRAWINGS

The objects and advantages of the invention will become apparent from the following detailed description of the preferred embodiments thereof in connection with the accompanying drawings, in which like numerals designate like elements, and in which.

DETAILED DESCRIPTION OF PREFERRED EMBODIMENTS OF THE INVENTION

Figure 1:
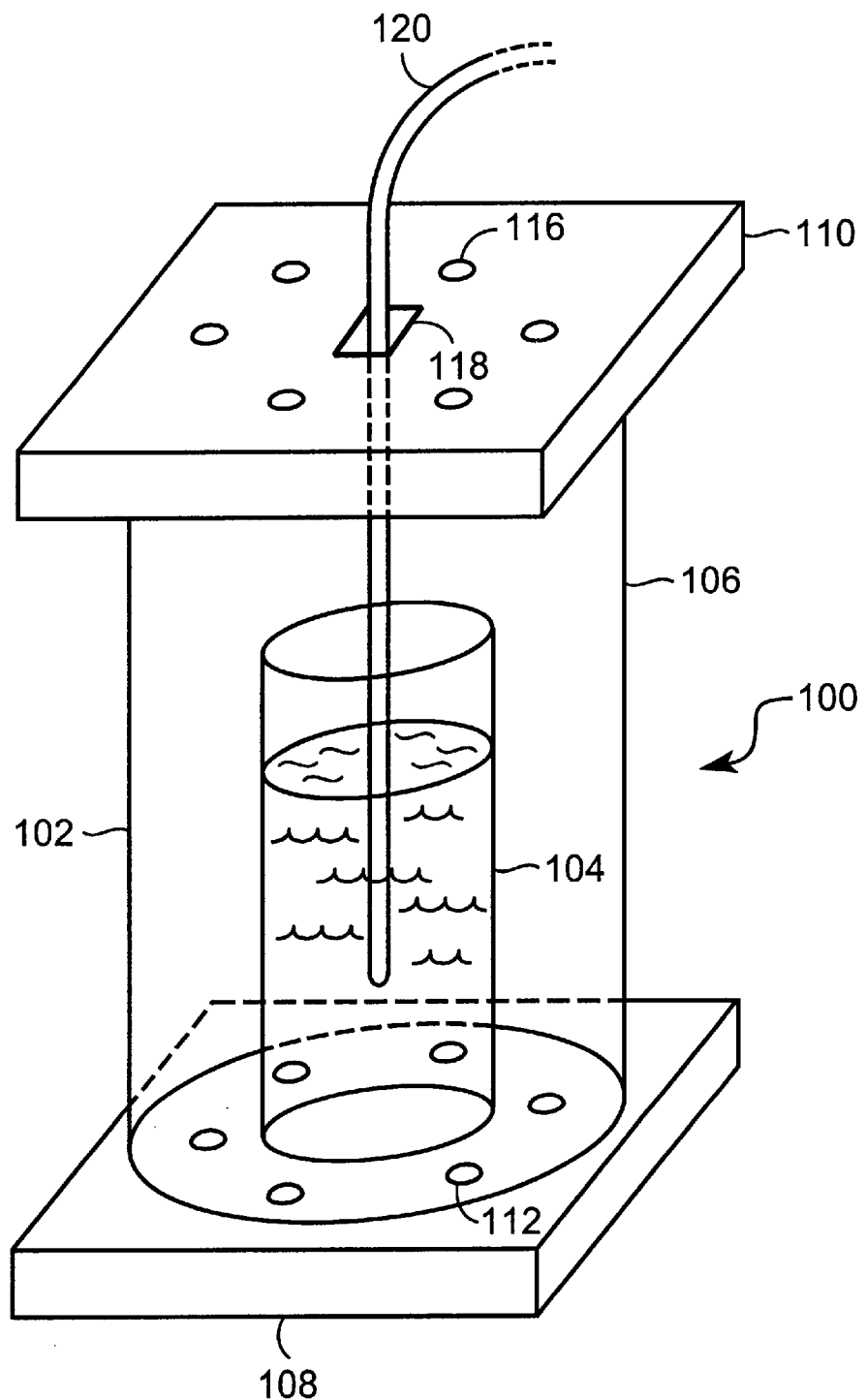
FIG. 1 illustrates an exemplary apparatus for preparing a liquid sample in accordance with the invention.

The invention will now be described with reference to FIG. 1, which illustrates an apparatus 100 for preparing a liquid sample in accordance with the invention. It should be clear that the illustrated apparatuses are merely exemplary.

The invention has particular application in the preparation of a liquid sample to be introduced into an analytical instrument. Examples of such instruments include liquid chromatographs (LC), for example, an ion chromatograph (IC) or a high-pressure liquid chromatograph (HPLC), gas chromatographs (GC) and solid-phase-extraction (SPE) instruments. The invention is, of course, not limited to such applications. The invention can be applied, for example, to any situation in which a high-purity liquid chemical is being transported pneumatically from a pressurizable vessel, wherein the pneumatic (pressurizing) gas contacts the liquid chemical.

The apparatus includes a pressurizable vessel 102, which houses a liquid-sample container 104, which contains a liquid chemical. The pressurizable vessel includes a cylindrical side wall 106, which sits on a lower stage 108. A lid 110 is disposed on the cylindrical side wall 106. The material of construction for these parts is typically a plastic such as PVC or polypropylene. It should be clear that the illustrated configuration of the pressurizable vessel is merely exemplary. For example, the vessel need not be cylindrical but can take other shapes and forms, such as a cubic or other box-like shape.

Figure 2:
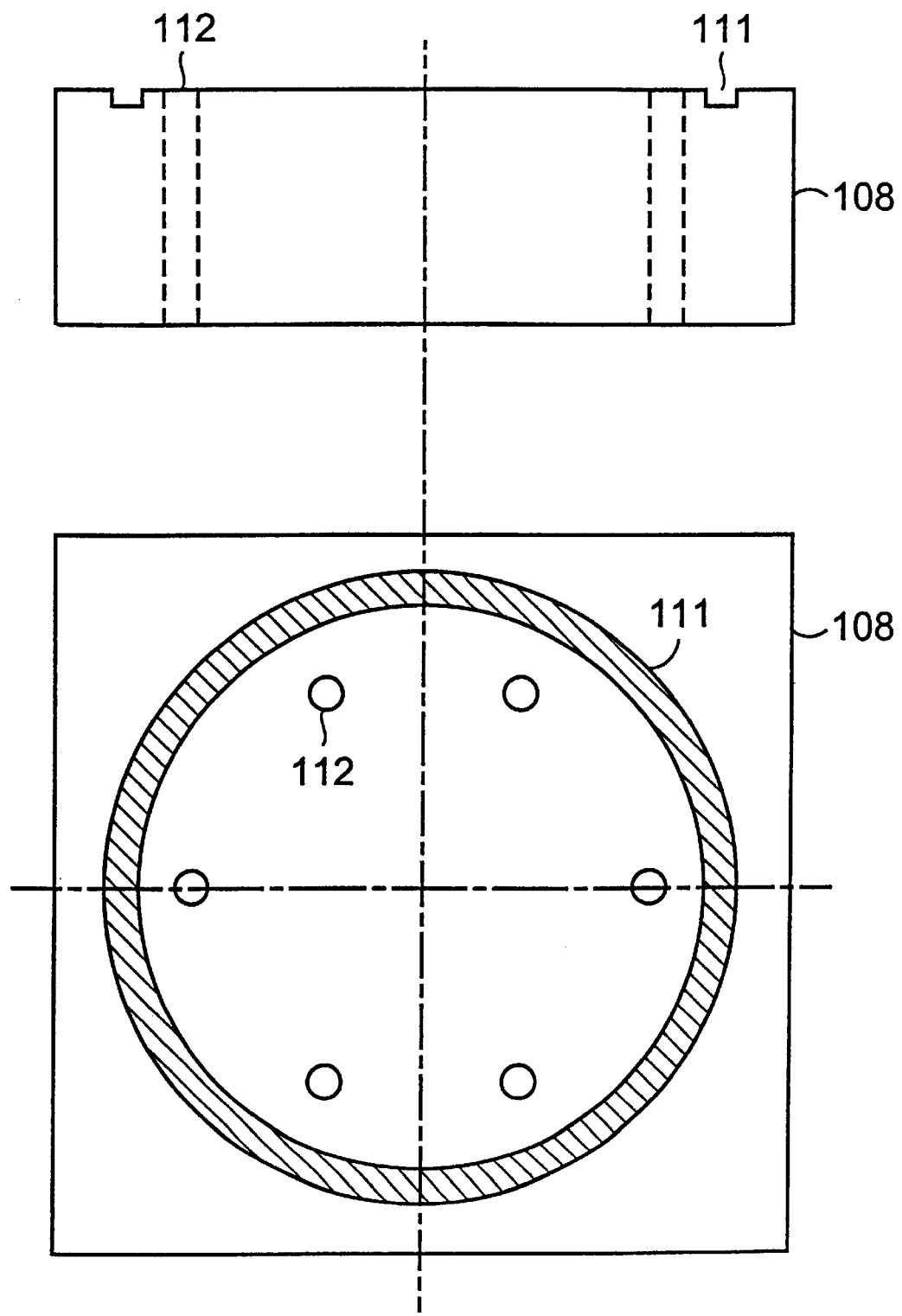
FIG. 2 is a cross-sectional and top-down view of a vessel sample stage, which forms a portion of the exemplary apparatus for preparing a liquid sample in accordance with the invention.

FIG. 2 illustrates the lower stage 108 in cross-sectional and top-down views. The lower stage includes a groove 111 for receiving the bottom of the cylindrical side wall 106. One or more apertures 112 (six shown) are provided in the lower-stage portion and serve as either a purge-gas inlet or a purge-gas outlet, depending on whether they are connected to a gas source or exhaust line.

Figure 3:
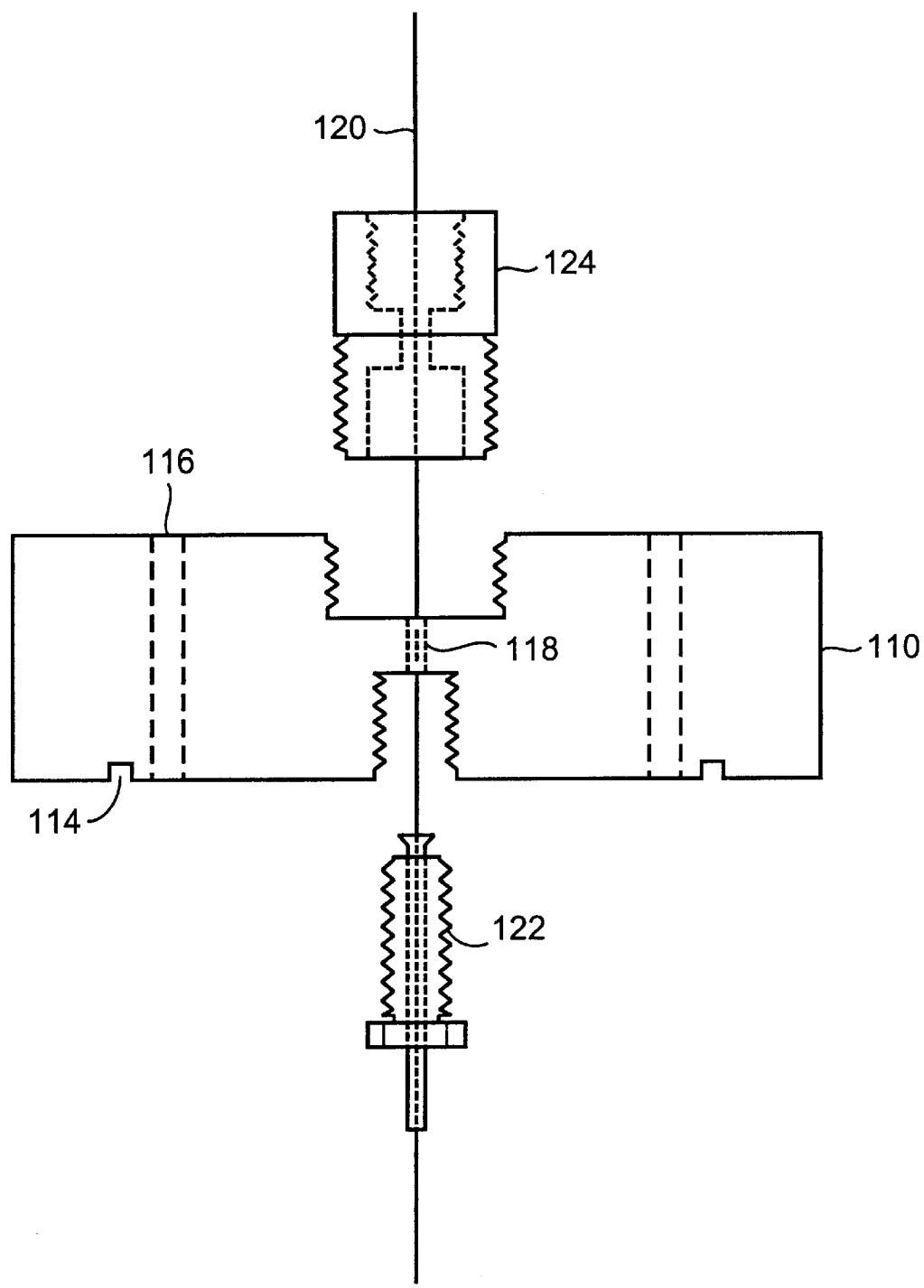
FIG. 3 is an exploded cross-sectional view of a vessel lid, which forms a portion of the exemplary apparatus for preparing a liquid sample in accordance with the invention.

FIG. 3 is an exploded cross-sectional view of the lid 110 of the pressurizable vessel. Like the lower stage, the lid includes a groove 114 for receiving the top of the cylindrical side wall 106. One or more apertures 116 (the number typically matching that for the stage 108) are provided in the lid. These apertures serve as the other of the purge-gas outlet or purge-gas inlet, depending on the function of the apertures 112 in the lower stage. The lid portion further includes an aperture 118 through its axis for feeding therethrough a sample tube 120, which runs from the liquid-sample container to, for example, the analytical-instrument inlet (not shown). The sample-tube material will depend on the particular liquid chemical passing therethrough. Typical materials include, for example, PEEK (polyether ether ketone).

The number, size and design of the gas-inlet and -outlet apertures can take various forms, with a primary consideration being effectiveness in purging out the atmosphere in the vessel. For example, the apertures can be formed in sidewalls of the vessel. The inlet apertures are typically equal in number to the outlet apertures and disposed opposite one another, since this arrangement provides effective purging. At a minimum, a single purge-gas-inlet aperture and a single purge-gas-outlet aperture are provided. The aperture diameter will depend primarily on the inner diameter of the purge-gas tubing. Typical aperture and tubing diameters are from about 1/16 to 1/8 inch, for example, about 1/16 inch.

Threaded fittings 122, 124 can be provided for ensuring a substantially leaktight seal where the sample tube passes through the lid. The use of such fittings is described in the above-cited L. Vanatta, J. Chromatogr. A 739 (1996), pp. 199–205. The fittings are typically a plastic, for example, polypropylene or PEEK.

Figure 4:
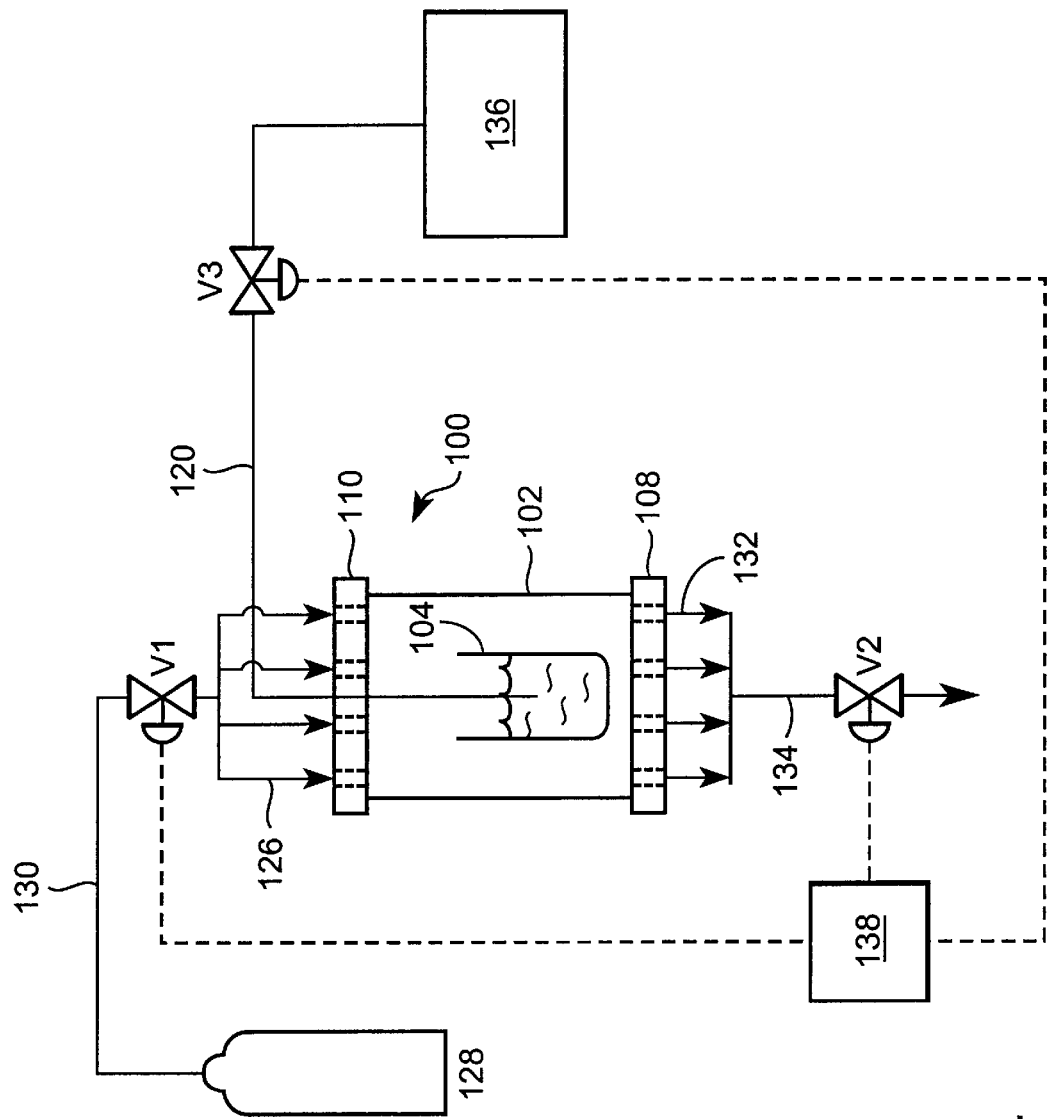
FIG. 4 illustrates an exemplary apparatus for preparing a liquid sample in accordance with a further aspect of invention.

FIG. 4 illustrates an exemplary apparatus for delivery of a liquid sample, which apparatus includes the above-described pressurizable vessel 102.

The purge-gas inlet apertures can each be connected to a gas-inlet conduit 126, which is typically fed from a common source 128 of pure purge gas such as helium, nitrogen or argon. Typically, the gas-inlet conduits 126 branch off of a single conduit 130, which includes a shutoff valve.

Similarly, the purge-gas outlet apertures can each be connected to a gas-outlet conduit 132, all of which can join to form a single exhaust line 134. Typically, the purge-gas outlet conduits are connected to a house exhaust, for example, through a fume hood.

Alternative to the illustrated example, a single gas-inlet conduit and/or a single gas-outlet conduit can be used, even in the situation of plural gas-inlet and/or gas-outlet apertures. This arrangement can be accomplished, for example, by provision of a gas-inlet plenum (not shown) and/or a gas-outlet plenum (not shown) in the pressurizable vessel. In such case, the plural apertures can be provided in plenum wall(s) facing the interior of the vessel.

The purge-gas inlet and -outlet conduits 126 and 132, respectively, can be formed from stainless-steel tubing, for example, RA15, or from a soft plastic tubing such as polyurethane or TEFLON. A typical inner diameter is from about $1/16$ to $1/8$ inch, for example, about $1/16$ inch. These conduits can be connected to the inlet and outlet apertures of the vessel 102 by, for example, Swagelok fittings (for stainless-steel tubing), or barbed-PEEK or -polypropylene fittings (for plastic tubing).

The sample tube 120, which includes a valve V3, is connected directly or indirectly to an analytical instrument 136, another use point, or even another container for holding the liquid sample.

The purge-gas and liquid-sample-distribution systems, including the valves and any other flow-control devices, are preferably automatically controlled by one or more controllers 138, which can take various forms, for example, a programmable logic controller (PLC) or other types of logic controllers. While a single controller has been shown connected to the valves, it should be clear to persons skilled in the art that plural controllers can be used to achieve the desired functions. The controller can actuate the valves, for example, based on a predetermined timing sequence.

An exemplary method of the invention will now be discussed, with reference to previously discussed drawing figures. A liquid sample is first introduced into the liquid-sample container 104, which is then placed in the pressurizable vessel 102. Valves V1 and V2 are opened, thereby allowing the purge gas to enter the pressurizable vessel through purge-gas inlet conduits 126 and apertures 116. The atmosphere inside vessel 102 is displaced by the purge gas and exits the vessel with the purge gas through apertures 112 in lower stage 108, and gas-outlet conduits 132. As described above with reference to FIG. 1, the direction of the purge-gas flow can be the reverse of that illustrated.

After a predetermined period of time has elapsed, which time is sufficient for the atmosphere in the vessel to be displaced by the purge gas, for example, five minutes or more, valve V2 is closed.

With valve V1 open and V2 closed, the purge-gas flow into vessel 102 is continued until a predetermined pressure in the vessel is attained, thereby pressurizing the vessel for transfer of the liquid sample as needed. Typically, the purge gas is introduced at a pressure of from about 80 to 100 psig. The liquid sample is transferred from vessel 102 through sample tube 120 to an analytical instrument 136, another use point, or another container for holding the liquid sample.

While the invention has been described in detail with reference to specific embodiments thereof, it will be apparent to one skilled in the art that various changes and modifications can be made, and equivalents employed, without departing from the scope of the appended claims.

What is claimed is:

1. A method of preparing a liquid sample, comprising:
providing a pressurizable vessel that contains a liquid sample in a container, and a sample tube extending from beneath the surface of the liquid sample to a point outside of the vessel;
introducing a purge gas into the vessel through a purge-gas inlet conduit, and simultaneously removing the gas atmosphere in the vessel through a purge-gas outlet conduit, thereby displacing the atmosphere in the pressurizable vessel; and
pressurizing the vessel with the purge gas to transfer a portion of the liquid sample from the container through the sample tube.

2. The method of claim 1, wherein the purge gas is helium, argon or nitrogen.

3. The method of claim 2, wherein the purge gas is helium.

4. A method of performing an analytical measurement, comprising:
providing a pressurizable vessel that contains a liquid sample in a container, and a sample tube extending from beneath the surface of the liquid sample to an analytical instrument;
introducing a purge gas into the vessel through a purge-gas inlet conduit, and simultaneously removing the gas atmosphere in the vessel through a purge-gas outlet conduit, thereby displacing the atmosphere in the pressurizable vessel;
pressurizing the vessel with the purge gas to transfer a portion of the liquid sample from the container through the sample tube; and
introducing the liquid sample into the analytical instrument.

5. The method of claim 4, wherein the purge gas is helium, argon or nitrogen.

6. The method of claim 5, wherein the purge gas is helium.

7. The method of claim 4, wherein the analytical instrument is a liquid chromatograph.

8. The method of claim 4, wherein the analytical instrument is a gas chromatograph.

9. The method of claim 4, wherein the analytical instrument is a solid-phase-extraction instrument.

10. An apparatus for preparing a liquid sample, comprising:
a pressurizable vessel comprising one or more walls, and a plurality of apertures in the walls, the apertures comprising one or more purge-gas inlet apertures and one or more purge-gas outlet apertures;
one or more purge-gas inlet conduits connected to the pressurizable vessel in fluid communication with the purge-gas inlet apertures, for introducing a purge gas through the purge-gas inlet apertures;
a liquid-sample container for holding a liquid sample inside the pressurizable vessel; and
a sample tube extending from beneath the surface of the liquid-sample in the container to a point outside of the pressurizable vessel for pneumatically transferring the liquid sample from the liquid-sample container to the point outside of the pressurizable vessel.

11. The apparatus according to claim 10, further comprising one or more purge-gas outlet conduits connected to the pressurizable vessel, in fluid communication with the purge-gas outlet apertures, for removing the gas atmosphere from the pressurizable vessel.

12. The apparatus of claim 10, wherein the purge-gas inlet apertures are disposed across the pressurizable vessel from the purge-gas outlet apertures.

13. The apparatus of claim 10, wherein the walls of the pressurizable vessel comprise:

one or more sidewalls;

a vessel lid forming a top wall of the vessel; and a stage forming a bottom wall of the vessel.

14. The apparatus of claim 13, wherein the lid is removable, allowing the sample container to be loaded into the vessel.

15. The apparatus of claim 13, wherein the one or more purge-gas inlet apertures or the one or more purge-gas outlet apertures are disposed in the lid.

16. The apparatus of claim 15, wherein a plurality of the purge-gas inlet apertures or the purge-gas outlet apertures are present in the lid.

17. The apparatus of claim 15, wherein the other of the one or more purge-gas inlet apertures or the one or more purge-gas outlet apertures are disposed in the stage.

18. The apparatus of claim 17, wherein a plurality of the purge-gas inlet apertures or the purge-gas outlet apertures are present in the lid, and a plurality of the other of the purge-gas inlet apertures or the purge-gas outlet apertures are present in the stage.

19. The apparatus of claim 17, wherein the lid further comprises an aperture through which the sample tube passes.

20. The apparatus of claim 19, wherein the pressurizable vessel is cylindrical in shape.

21. An apparatus for performing an analytical measurement, comprising:

an analytical instrument;

and a pressurizable vessel comprising one or more walls, a plurality of apertures in the walls, the apertures comprising one or more purge-gas inlet apertures and one or more purge-gas outlet apertures;

one or more purge-gas inlet conduits connected to the pressurizable vessel in fluid communication with the purge-gas inlet apertures, for introducing a purge gas through the purge-gas inlet apertures;

a liquid-sample container for holding a liquid sample inside the pressurizable vessel; and a sample tube extending from beneath the surface of the liquid sample in the container to the analytical instrument.

22. The apparatus according to claim 21, further comprising one or more purge-gas outlet conduits connected to the pressurizable vessel, in fluid communication with the purge-gas outlet apertures, for removing the gas atmosphere from the pressurizable vessel.

23. The apparatus of claim 21, wherein the purge-gas inlet apertures are disposed across the pressurizable vessel from the purge-gas outlet apertures.

24. The apparatus of claim 21, wherein the walls of the pressurizable vessel comprise:

one or more sidewalls;

a vessel lid forming a top wall of the vessel; and a stage forming a bottom wall of the vessel.

25. The apparatus of claim 24, wherein the lid is removable, allowing the sample container to be loaded into the vessel.

26. The apparatus of claim 24, wherein the one or more purge-gas inlet apertures or the one or more purge-gas outlet apertures are disposed in the lid.

27. The apparatus of claim 26, wherein a plurality of the purge-gas inlet apertures or the purge-gas outlet apertures are present in the lid.

28. The apparatus of claim 26, wherein the other of the one or more purge-gas inlet apertures or the one or more purge-gas outlet apertures are disposed in the stage.

29. The apparatus of claim 28, wherein a plurality of the purge-gas inlet apertures or the purge-gas outlet apertures are present in the lid, and a plurality of the other of the purge-gas inlet apertures or the purge-gas outlet apertures are present in the stage.

30. The apparatus of claim 28, wherein the lid further comprises an aperture through which the sample tube passes.

31. The apparatus of claim 30, wherein the pressurizable vessel is cylindrical in shape.

32. The apparatus of claim 21, wherein the analytical instrument is a liquid chromatograph.

33. The apparatus of claim 21, wherein the analytical instrument is a gas chromatograph.

34. The apparatus of claim 21, wherein the analytical instrument is a solid phase-extraction instrument.

* * * * *

UNITED STATES PATENT AND TRADEMARK OFFICE
CERTIFICATE OF CORRECTION

PATENT NO.    : 6,684,721 B2
DATED         : February 3, 2004
INVENTOR(S)   : Lynn Vanatta It is certified that error appears in the above-identified patent and that said Letters Patent is hereby corrected as shown below:

Column 7,
Line 35, please remove the word "and" at the beginning of the line.
Line 36, please add the word "and" at the beginning of the line.

Signed and Sealed this

Sixth Day of July, 2004

JON W. DUDAS
*Acting Director of the United States Patent and Trademark Office*